(12) United States Patent
Liu et al.

(10) Patent No.: US 7,411,003 B1
(45) Date of Patent: Aug. 12, 2008

(54) **INHIBITION OF HEPATITIS B VIRUS BY CYCLOHEXENONE COMPOUNDS FROM *ANTRODIA CAMPHORATA***

(75) Inventors: Sheng-Yun Liu, Taipei Hsien (TW); Mao-Tien Kuo, Taipei Hsien (TW); Wu-Che Wen, Taipei Hsien (TW)

(73) Assignee: Golden Biotechnology Corporation, Taipei Hsien (TW)

( * ) Notice: Subject to any disclaimer, the term of this patent is extended or adjusted under 35 U.S.C. 154(b) by 0 days.

(21) Appl. No.: 11/842,795

(22) Filed: Aug. 21, 2007

(30) Foreign Application Priority Data

Jul. 9, 2007 (TW) .............................. 96124892 A

(51) Int. Cl.
*A61K 31/12* (2006.01)
*C07C 49/543* (2006.01)

(52) U.S. Cl. ...................................... 514/690; 568/377
(58) Field of Classification Search ........................ None
See application file for complete search history.

(56) References Cited

OTHER PUBLICATIONS

Shu-Wei Yang et al., "Steroids and Triterpenoids of *Antrodia cinnamomea*-A Fungus Parasitic on *Cinnamomum micranthum*," Phytochemistry, vol. 41, No. 5, pp. 1389-1392, 1996.

I-Hwa Chering et al., "Triterpenoids from *Antrodia cinnamomea*," Phytochemistry, vol. 41, No. 1, pp. 263-267, 1996.

Hung-Chen Chiang et al., "A Sesquiterpene Lactone, Phenyl and Biphenyl Compounds from *Antrodia cinnamomea*," Phytochemistry, vol. 39, No. 3, pp. 613-616, 1995.

I-Hwa Chering et al., "Three New Triterpenoids From *Antrodia cinnamomea*," Journal of Natural Products, vol. 58, No. 3, pp. 365-371, Mar. 1995.

Chung-Hsiung et al.,"New Steroid Acids From *Antrodia cinnamomea*, A Fungal Parasite of *Cinnamomum micranthum*," Journal of Natural Products, vol. 58, No. 11, pp. 1655-1661, Nov. 1995.

Mary Ann Sells et al., "Production of Hepatitis B Virus Particles in HEP G2 Cells Transfected With Cloned Hepatitis B Virus DNA," Proc. Natl. acad. Sci. USA, vol. 84, 1005-1009, Feb. 1987.

*Primary Examiner*—Sikari A Witherspoon
(74) *Attorney, Agent, or Firm*—Birch Stewart Kolasch & Birch, LLP

(57) ABSTRACT

The present invention relates to a compound of *Antrodia camphorata* used to inhibit HBV, in particular to an extract, 4-hydroxy-2,3-dimethoxy-6-methyl-5(3,7,11-trimethyl-dodeca-2,6,10-trienyl)-cyclohex-2-enone which is isolated from *Antrodia camphorata*, and its use in inhibiting HBV effectively. The cyclohexenone compound according to the present invention showed cytotoxicity on HBV-secreting human hepatoma cell line HepG2 2.2.15, decreased synthesis of HBV particles, further inhibited synthesis of HbsAg and HbeAg effectively to achieve the goal of HBV inhibition.

12 Claims, 3 Drawing Sheets

A.

B.

A.

B.

A.

B.

INHIBITION OF HEPATITIS B VIRUS BY CYCLOHEXENONE COMPOUNDS FROM *ANTRODIA CAMPHORATA*

BACKGROUND OF THE INVENTION

1. Field of the Invention

The present invention relates to an anti-viral compound, in particular to a cyclohexenone compound isolated and purified from *Antrodia camphorata* extracts and can be applied in inhibition of hepatitis B virus.

2. The Prior Arts

The Hepatitis B Virus (HBV) is a small double-stranded, enveloped virus of the Hepadnviridae family, which causes sustained noncytopathic liver infection. It is the only DNA virus among all human liver viruses. The membrane of hepatitis B virus composed of 25% lipid and 75% glycoprotein. The major component for glycoprotein is hepatitis B surface antigen (HbsAg). Core region of HBV particle contains hepatitis B envelop antigen (HbeAg). HBeAg is a secretory protein which can pass through human placenta from mother to fetus in early stage, and elicits cytotoxic T-cells tolerance to HbeAg due to immature immune systems in babies. The immune system in human can not clear HBV and causes high-level HBV replication. HBeAg is also considered as a tolergen. Therefore, the levels of HBsAg and HBeAg can be used as markers of hepatitis for evaluating the HBV replication and secretion. The World Health Organization indicated that about two billion people show evidence of past or current infection with HBV, which has a high prevalence and incidence rate. Vertical transmission is the main path of HBV infection. The virus can cause acute hepatitis, chronic hepatitis, and liver cirrhosis, even developed to liver cancer. Around 90% of the males above 30 years old in Taiwan were infected with HBV. 15% to 20% of them become life-long carriers, and may die from sequelae including liver cirrhosis and liver cancer. Therefore Taiwan is a hyperendemic area for HBV infection and liver cancer.

The HBV infection is closed related to liver diseases and liver cancer as mentioned above. Anti-viral therapy through interference and inhibition of viral replication, and elimination of chronic infection is the major purpose for the related studies. Treatments with interferon, anti-viral drugs or vaccines show beneficial effects recently. However, chronic carriers of hepatitis B can not be cured completely; this is the main reason for HBV related liver diseases and high mortality. Therefore, development of HBV inhibiting anti-viral drugs is crucial at present.

*Antrodia camphorata* is also called Chang-Zhi, Niu Chang-Zhi, red camphor mushroom and the like, which is a perennial mushroom belonging to the order Aphyllophorales, the family Polyporaceae. It is an endemic species in Taiwan growing on the inner rotten heart wood wall of *Cinnamomum kanehirai* Hay. *Cinnamoum kanehirai* Hay is rarely distributed and being overcut unlawfully, which makes *Antrodia camphorata* growing inside the tree in the wild became even rare. The price of *Antrodia camphorata* is very expensive due to the extremely slow growth rate of natural *Antrodia camphorata* that only grows between Junes to October.

The fruiting bodies of *Antrodia camphorata* are perennial, sessile, hard and woody, which exhales strong smell of sassafras (camphor aroma). The appearances are various with plate-like, bell-like, hoof-like, or tower-like shapes. They are reddish in color and flat when young, attached to the surface of wood. Then the brims of the front end become little curled tilted and extend to the surroundings. The color turns to be faded red-brown or cream yellow brown, with ostioles all over. This region is of very high medical value.

In traditional Taiwanese medicine, *Antrodia camphorata* is commonly used as an antidotal, liver protective, anti-cancer drug. *Antrodia camphorata*, like general edible and medicinal mushrooms, is rich in numerous nutrients including polysaccharides (such as β-glucosan), triterpenoids, superoxide dismutase (SOD), adenosine, proteins (immunoglobulins), vitamins (such as vitamin B, nicotinic acid), trace elements (such as calcium, phosphorus and germanium and so on), nucleic acid, agglutinin, amino acids, steroids, lignins and stabilizers for blood pressure (such as antodia acid) and the like. These physiologically active ingredients are believed to exhibit effects such as: anti-tumor activities, increasing immuno-modulating activities, anti-allergy, anti-bacteria, anti-high blood pressure, decreasing blood sugar, decreasing cholesterol and the like.

Triterpenoids are the most studied component among the numerous compositions of *Antrodia camphorata*. Triterpenoids are the summary terms for natural compounds, which contain 30 carbon atoms with the pent acyclic or hex acyclic structures. The bitter taste of *Antrodia camphorata* is from the component of triterpenoids. Three novel ergostane-type triterpenoids (antcin A, antcin B, antcin C) were isolated by Cherng et al. from the fruiting bodies of *Antrodia camphorata* (Cherng, I. II., and Chiang, II. C. 1995. Three new triterpenoids from *Antrodia cinnamomea*. J. Nat. Prod. 58:365-371). Three new compounds zhankuic acid A, zhankuic acid B and zhankuic acid were extracted from the fruiting bodies of *Antrodia camphorata* with ethanol by Chen et al. (Chen, C. H., and Yang, S. W. 1995. New steroid acids from *Antrodia cinnamomea*,—a fungus parasitic on *Cinnamomum micranthum*, J. Nat. Prod. 58:1655-1661). In addition, Cherng et al. also found three other new triterpenoids from the fruiting bodies of *Antrodia camphorata*, which are sesquiterpene lactone and 2 biphenyl derived compounds, 4,7-dimethoxy-5-methy-1,3-benzodioxole and 2,2',5,5'-teramethoxy-3,4,3',4'-bi-methylenedioxy-6,6'-dimethylbiphenyl (Chiang, H. C., Wu, D. P., Cherng, I. W., and Ueng, C. H. 1995. A sesquiterpene lactone, phenyl and biphenyl compounds from *Antrodia cinnamomea*. Phytochemistry, 39:613-616). In 1996, four novel ergostane-type triterpenoids (antcins E and F and methyl antcinates G and H) were isolated by Cherng et al. with the same analytic methods (Cherng, I. H., Wu, D. P., and Chiang, H. C. 1996. Triteroenoids from *Antrodia cinnamomea*. Phytochemistry. 41:263-267). And two ergostane related steroids, zhankuic acids D and E together with three lanosta related triterpenes, 15 alpha-acetyl-dehydrosulphurenic acid, dehydroburicoic acid, dehydrosulphurenic acid were isolated by Yang et al. (Yang, S. W., Shen, Y. C., and Chen, C. H. 1996. Steroids and triterpenoids of *Antrodia cinnamomea*—a fungus parasitic on *Cinnamomum micranthum*. Phytochemistry. 41:1389-1392).

Although *Antrodia camphorata* extracts were reported to have the abovementioned effects from the previous experiments, and the components were analyzed in succession, further experiments are needed to identify the effective composition to inhibit HBV infection and to treat the HBV-related liver diseases. The natural components of *Antrodia camphorata* extracts will greatly contributes great beneficial effects in treating HBV-related liver diseases include acute hepatitis, chronic hepatitis, liver cirrhosis, and liver cancer if the real effective composition is found.

SUMMARY OF THE INVENTION

In order to identify which are the compounds to inhibit HBV infection from the extracts of *Antrodia camphorata*, the compound of the formula (1) was isolated and purified in the present invention,

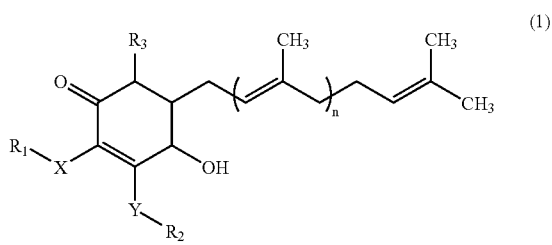

(1)

wherein X and Y can be oxygen or sulfur, $R_1$, $R_2$ and $R_3$ are each a hydrogen atom, methyl or $(CH_2)_m$—$CH_3$ and m=1-12; n=1-12.

A preferred compound of the general formula (1) is 4-hydroxy-2,3-dimethoxy-6-methyl-5(3,7,11-trimethyl-dodeca-2,6,10-trienyl)-cyclohex-2-enone as shown in formula (2), with molecular formula of $C_{24}H_{38}O_4$, appearance of pale yellow powder and molecular weight of 390.

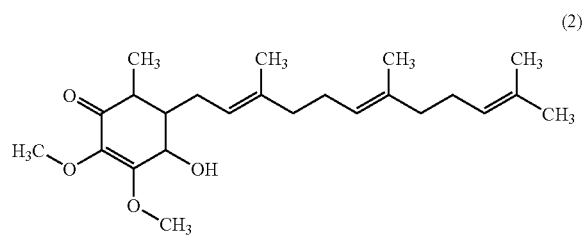

(2)

Cyclohexenone compounds having the structures of formula (1) and formula (2) are purified from aqueous extraction or organic solvent extraction of *Antrodia camphorata*. The organic solvents used include, but not limited to, alcohols such as methanol, ethanol or propanol, esters such as ethyl acetate, alkanes such as hexane, or halogenated alkanes such as chloromethane, chloroethane. Among them, alcohol is preferred, and ethanol is particularly preferred.

Cyclohexenone compounds of the present invention are applied in inhibiting HBV infection, which can further be applied in pharmaceutical compositions for treating hepatitis B-related liver diseases in order to enhance therapeutic effects in acute hepatitis, chronic hepatitis, liver cirrhosis and liver cancer. It is concluded that treatment of an HepG2 2.2.15 cell line producing infectious HBV particles with the formula (1) or the formula (2) of the invention not only inhibited the relative survival rate of the hepatoma cell line, but also decreased the replication and secretion of HbsAg and HbeAg. In addition, the natural substance of this compound extracted from *Antrodia camphorata* can be used to treat hepatitis B-related liver diseases.

On the other hand, the compounds of formula (1) and/or formula (2) in the present invention can be incorporated into pharmaceutical compositions for treating hepatitis B-related liver diseases to inhibit the replication and secretion of HBV, further to alleviate infection of acute hepatitis or chronic hepatitis, and to decrease the incident rate for transformation of carriers into liver cirrhosis, or the death rate of liver cancer.

The pharmaceutical compositions include not only the compounds of formula (1) and/or formula (2), but also the pharmaceutically accepted carries. Examples of such carriers include, but are not limited to, excipients such as water, fillers such as sucrose or starch, binders such as cellulose derivatives, diluents, disintegrants, absorption enhancers or sweeteners. The pharmaceutical composition can be manufactured through mixing the compounds of formula (1) and/or formula (2) with at least one of the carriers by means of conventional methods known in the pharmaceutically technical field, which can be formulated in the form of, but are not limited to, powder, tablets, capsules, pellets, granules or other liquid formulation.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

Figure 1:
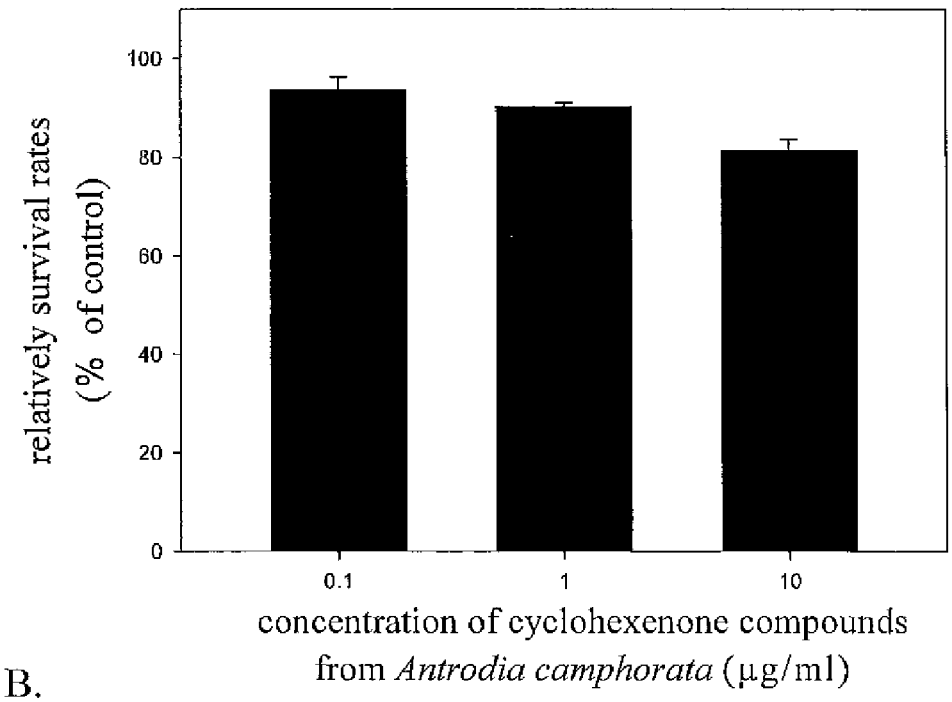
FIG. 1 The effects of 4-hydroxy-2,3-dimethoxy-6-methyl-5(3,7,11-trimethyl-dodeca-2,6,10-trienyl)-cyclohex-2-enone purified from example 1 of the present invention on survival rates of the HepG2 2.2.1 cells. (A) 4-hydroxy-2,3-dimethoxy-6-methyl-5(3,7,11-trimethyl-dodeca-2,6,10-trienyl)-cyclohex-2-enone; (B) crude extracts of *Antrodia camphorata*. Vertical lines represent standard deviation of three independent tests.
Figure 1:
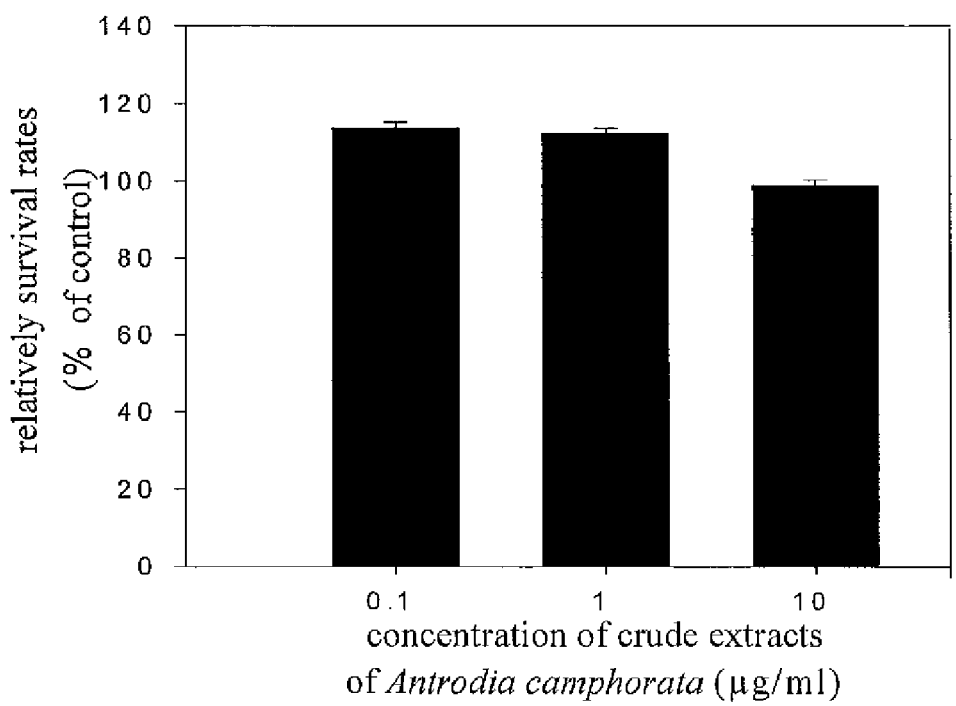

The mycelia, fruiting bodies or mixture of both from *Antrodia camphorata* are first extracted with water or organic solvents to obtain the aqueous extract or organic solvent extract of *Antrodia camphorata* using the methods well known in the arts. The organic solvents include, but not limited to, alcohols such as methanol; ethanol or propanol; esters such as Ethyl acetate; alkanes such as hexane; or halogenated alkanes such as chloromethane, and chloroethane. Among them, alcohol is preferred, and ethanol is particularly preferred.

The aqueous or organic solvent extracts of *Antrodia camphorata* were subjected to high-performance liquid chromatography (HPLC) for isolation and purification. Each fraction was recovered and applied to HBV replication assay. The potent fractions with HBV-inhibition effects were analyzed for the composition and further assayed with related biochemical tests such as cytotoxic effects on hepatoma cell line HepG2 2.2.15 and detection of the levels of HbsAg and HbeAg. The above approach then led to the identification of compounds of formula (1) and formula (2) in inhibiting HBV replication.

The compound 4-hydroxy-2,3-dimethoxy-6-methyl-5(3, 7,11-trimethyl-dodeca-2,6,10-trienyl)-cyclohex-2-enone of the formula (2) is explained below as an example for the present invention. Cytotoxic effects of 4-hydroxy-2,3-dimethoxy-6-methyl-5(3,7,11-trimethyl-dodeca-2,6,10-trienyl)-cyclohex-2-enone on HepG2 2.2.15 and HBV replication inhibiting effects were assessed using MTT [3-(4,5-dimethylthiazol-2-yl)-2,5-diphenyltetrazolium bromide] assay according to the anticancer-drug screening model of National Cancer Institute (NCI) to analyze survival rates on hepatoma cell line HepG2 2.2.15, and semi-quantitative enzyme immunoassay to detect HbsAg and HbeAg levels. These assays have proved that cyclohexenone from *Antrodia camphorata* can be used to decrease the survival rates of hepatoma cell line HepG2 2.2.15, effectively inhibit the synthesis of HbsAg and HbeAg and further to achieve the goals of inhibition of HBV replication and secretion. The details of the examples are described as follows:

EXAMPLE 1

Isolation of 4-hydroxy-2,3-dimethoxy-6-methyl-5(3, 7,11-trimethyl-dodeca-2,6,10-trienyl)-cyclohex-2-enone One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and a 0.45 µm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.1-0.5% acetic acid (B), with the gradient conditions of 0-10 min in 95%~20% B, 10-20 min in 20%~10% B, 20-35 min in 10%~10% B, 35-40 min in 10%~95% B, at the flow rate of 1 ml/min. The column effluent was monitored with a UV-visible detector.

The fractions collected at 25-30 min were collected and concentrated to yield 4-hydroxy-2,3-dimethoxy-6-methyl-5 (3,7,11-trimethyl-dodeca-2,6,10-trienyl)-cyclohex-2-enone, a product of pale yellow powder. The analysis of 4-hydroxy-2,3-dimethoxy-6-methyl-5(3,7,11-trimethyl-dodeca-2,6,10-trienyl)-cyclohex-2-enone showed the molecular formula of $C_{24}H_{38}O_4$, molecular weight of 390, melting point of 48° C.~52° C. Investigation of NMR spectra showed that $^1$H-NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (ppm)=12.31, 16.1, 16.12, 17.67, 25.67, 26.44, 26.74, 27.00, 39.71, 39.81, 4.027, 43.34, 59.22, 60.59, 120.97, 123.84, 124.30, 131.32, 135.35, 135.92, 138.05, 160.45, and 197.12.

EXAMPLE 2

In vitro Cytotoxic Tests on Hepatoma Cell Line with Cyclohexenone Compounds of *Antrodia camphorata*

Hepatoma cell inhibiting effects of cyclohexenone compounds of *Antrodia camphorata* from example 1 were assessed according to the anticancer-drug screening model of National Cancer Institute (NCI). The compound 4-hydroxy-2,3-dimethoxy-6-methyl-5(3,7,11-trimethyl-dodeca-2,6,10-trienyl)-cyclohex-2-enone from example 1 was added into the culture media of hepatoma cell line HepG2 2.2.15 to test the survival rates. Survival of cells was analyzed using MTT assay. HepG2 2.2.15 cell line was derived from human hepatoma, which can secrete infectious HBV.

MTT assay is commonly used to analyze cell proliferation, survival rate of viable cells and cytotoxicity. MTT (3[4,5-dimethylthiazol-2-yl]-2,5-diphenyltetrazolium bromide) is a yellow dye which can be converted to water-insoluble purple formazan on the reductive cleavage of its tetrazolium ring by the succinate tetrazolium reductase in mitrochondria of cells. The amount of formazan produced is used to detect the number of viable cells and calculate the survival rates.

The HepG2 2.2.1 cells were cultivated in minimum essential medium (MEM, Gibco Co., USA) containing 12 essential amino acids, glutamine, 8 vitamins, and supplemented with 10% fetal bovine serum and 200 µg/ml of antibiotic G418 for 24 hours. Amplified cells were washed once with PBS, treated with 1× trypsin-EDTA, and centrifuged at 1200 rpm for 5 min. The supernatant was removed and the cell pellet was resuspended in 10 ml of fresh medium by gently shaking. Cells were seeded onto 96-well plates at 5000 cells per well. Cells treated with the crude extracts of *Antrodia camphorata* prepared with DMSO (total ethanol extracts, not purified) were designed as the control group; and cells treated with 4-hydroxy-2,3-dimethoxy-6-methyl-5(3,7,11-trimethyl-dodeca-2,6,10-trienyl)-cyclohex-2-enone were designed as the experiment group. Both substrates were added in the concentration of 0.1, 1, 10 µg/ml respectively. Nothing was added to the blank-control group. Cells were cultivated at 37° C., 5% $CO_2$ for 22 hours. 2.5 mg/ml of MTT solution was added to each well and incubated in the dark for 2 hours. After careful removal of the MTT, the generated dark crystals were dissolved by 50 µl of DMSO. The absorbances were measured at 570 nm with an ELISA Reader and compared with that of the blank group to calculate the survival rates. The results are shown in FIG. 1.

Refers to FIG. 1, the effects of 4-hydroxy-2,3-dimethoxy-6-methyl-5(3,7,11-trimethyl-dodeca-2,6,10-trienyl)-cyclohex-2-enone purified from example 1 of the present invention on survival rates of the HepG2 2.2.1 cells. The compound 4-hydroxy-2,3-dimethoxy-6-methyl-5(3,7,11-trimethyl-dodeca-2,6,10-trienyl)-cyclohex-2-enone could effectively decrease the survival rates of the HepG2 2.2.1 cells in comparison to the crude extracts of *Antrodia camphorata* in control group, and the cell survival rates of 10 µg/ml of cyclohexenone from *Antrodia camphorata* could be lower than 81%. Therefore, it has been proved that the compound 4-hydroxy-2,3-dimethoxy-6-methyl-5(3,7,11-trimethyl-dodeca-2,6,10-trienyl)-cyclohex-2-enone could inhibit the growth of hepatoma cell line HepG2 2.2.1.

EXAMPLE 3

In vitro Tests on Secretion of HbsAg and HbeAg in the Hepatoma Cell Line with Cyclohexenone Compounds of *Antrodia camphorata*

The effects of cyclohexenone compounds of *Antrodia camphorata* purified from Example 1 on synthesis of HbsAg and HbeAg were tested in this example. The compound 4-hydroxy-2,3-dimethoxy-6-methyl-5(3,7,11-trimethyl-dodeca-2,6,10-trienyl)-cyclohex-2-enone from example 1 was added into the culture media of hepatoma cell line HepG2 2.2.1 to determine the synthesis of HbsAg and HbeAg with the semi-quantitative enzyme-linked immunoabsorbent assay (ELISA). These two makers were used to assess the effectiveness of cyclohexenone in HBV inhibition. HepG2 2.2.1 cell was formed by the transfection of Hep G2 cells with the complete HBV DNA, and was selected for resistance to antibiotic G418 and expression of HbsAg, HbeAg, nucleocapsid and virion (Sells, M. A., Chen, M. L. and Acs, G. 1987. Production of hepatitis B virus particles in HepG2 cells transfected with cloned hepatitis B virus DNA. Proc. Natl. Acad. Sci. USA. 84: 1005-1009).

Figure 2:
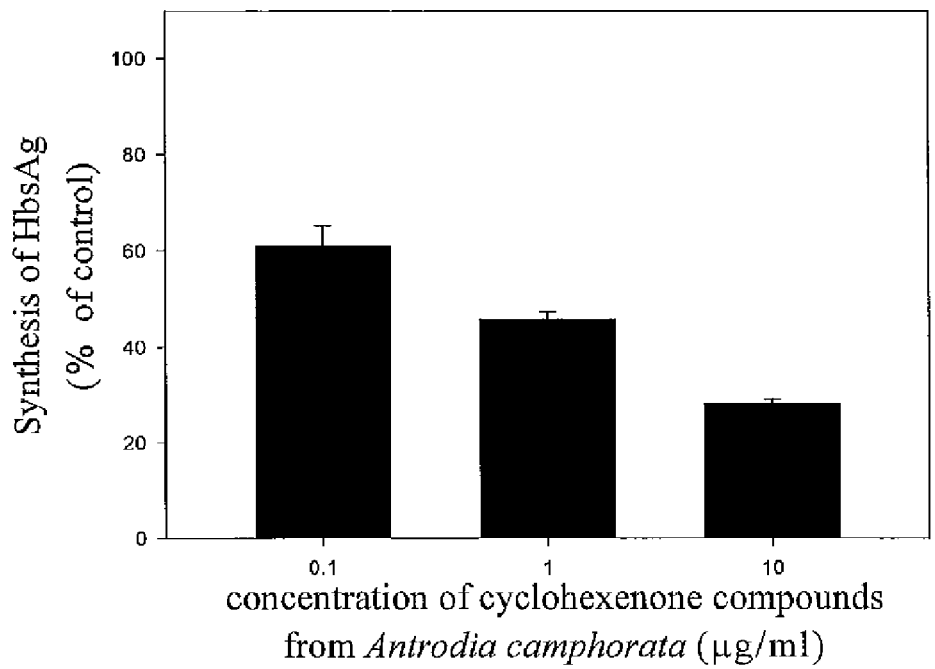
FIG. 2 The effects of 4-hydroxy-2,3-dimethoxy-6-methyl-5(3,7,11-trimethyl-dodeca-2,6,10-trienyl)-cyclohex-2-enone purified from example 1 of the present invention in synthesis of HbsAg. (A) 4-hydroxy-2,3-dimethoxy-6-methyl-5(3,7,11-trimethyl-dodeca-2,6,10-trienyl)-cyclohex-2-enone; (B) crude extracts of *Antrodia camphorata*. Vertical lines represent standard deviation of three independent tests.
Figure 2:
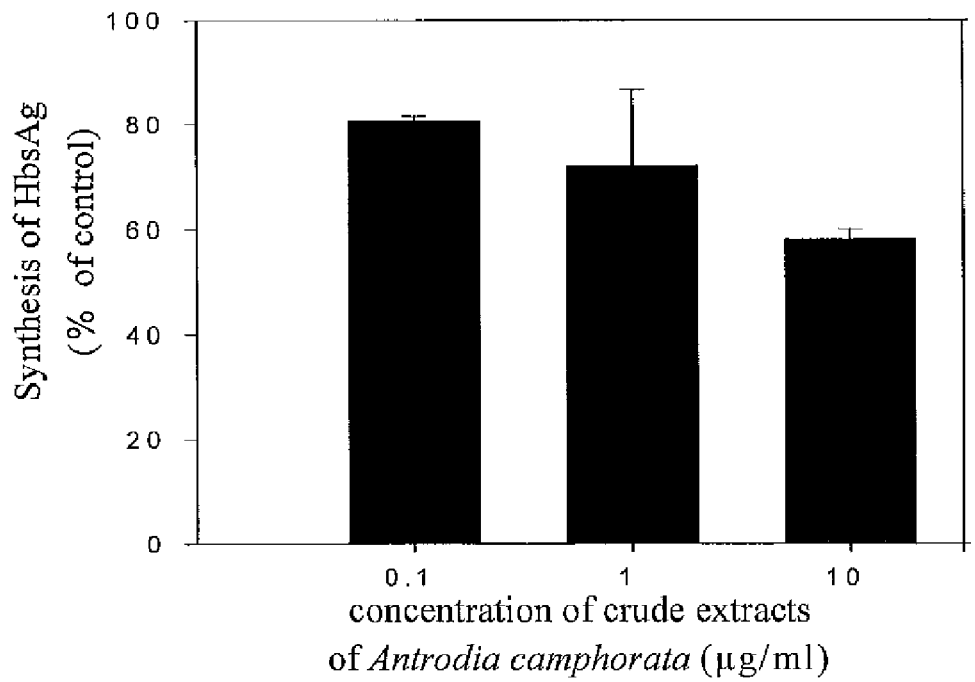

The HepG2 2.2.1 cells were cultivated in minimum essential medium (MEM, Gibco Co., USA) containing 12 essential amino acids, glutamine, 8 vitamins, and supplemented with 10% fetal bovine serum and 200 µg/ml of antibiotic G418 for 24 hours. Amplified cells were washed once with PBS, treated with 1× trypsin-EDTA, and centrifuged at 1200 rpm for 5 min. The supernatant was removed and the cell pellet was resuspended in 10 ml of fresh medium by gently shaking. Cells were seeded onto 96-well plates at 5000 cells per well. Cells treated with the crude extracts of *Antrodia camphorata* prepared with DMSO (total ethanol extracts, not purified) were designed as the control group; and cells treated with 4-hydroxy-2,3-dimethoxy-6-methyl-5(3,7,11-trimethyl-dodeca-2,6,10-trienyl)-cyclohex-2-enone were designed as the experiment group. Both substrates were added in the concentration of 0.1, 1, 10 µg/ml respectively. Nothing was added to the blank-control group. Cells were cultivated at 37° C., 5% $CO_2$ for 22 hours. Proper amounts of culture media were assayed for the levels of HbsAg and HbeAg with ELISA kit containing anti-HbsAg and anti-HbeAg monoclonal antibodies (General biologicals corp., Taiwan, ROC). The assay was based on formation of sandwich complexes of antibody-antigen-antibody/enzyme and stained with O-phenylenediamine (OPD) color development solution and the results were expressed as absorbance units at 450 nm. Specimens with absorbance values above the cut off value are taken as positive for HbsAg and HBeAg. The cutoff value=O.D. (blank)+ 0.025. The results are shown in FIG. 2 and FIG. 3.

Figure 3:
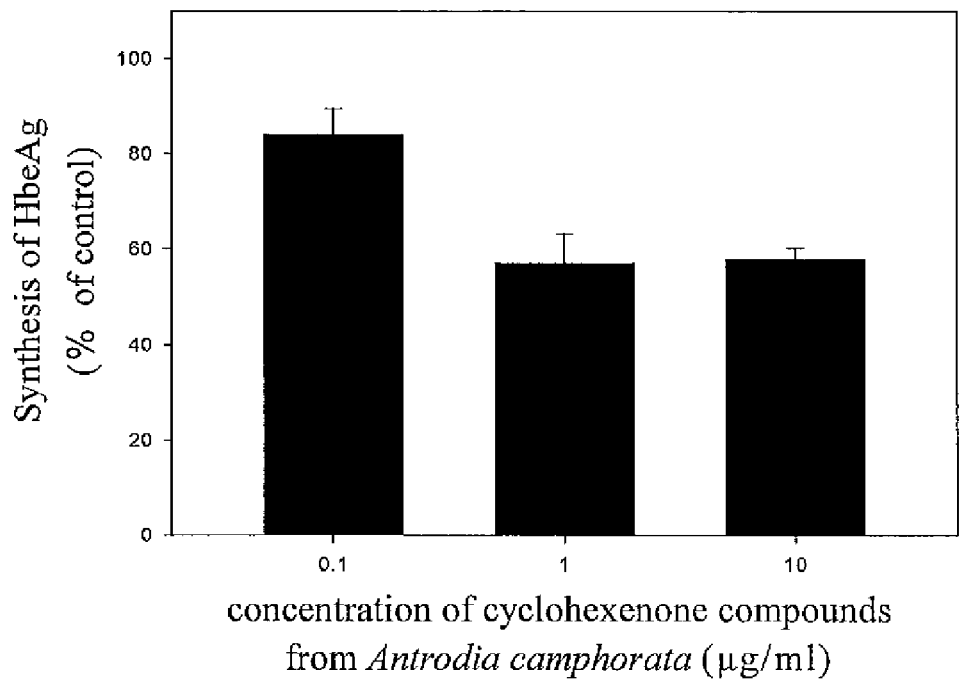
FIG. 3 The effects of 4-hydroxy-2,3-dimethoxy-6-methyl-5(3,7,11-trimethyl-dodeca-2,6,10-trienyl)-cyclohex-2-enone purified from example 1 of the present invention in synthesis of HbeAg. (A) 4-hydroxy-2,3-dimethoxy-6-methyl-5(3,7,11-trimethyl-dodeca-2,6,10-trienyl)-cyclohex-2-enone; (B) crude extracts of *Antrodia camphorata*. Vertical lines represent standard deviation of three independent tests.
Figure 3:
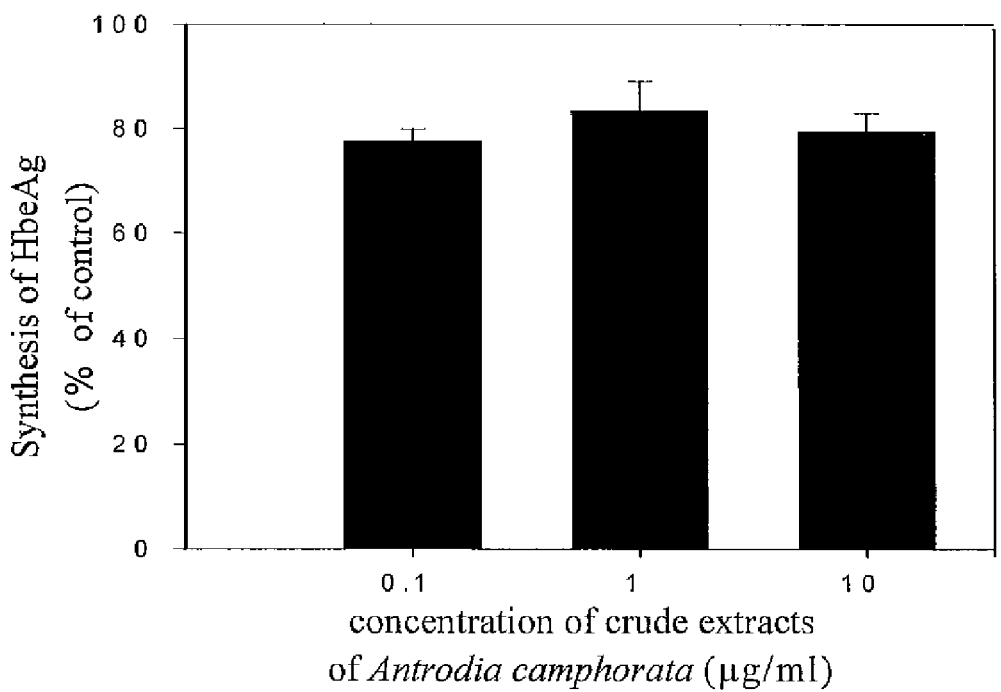

Refers to FIG. 3, the effects of 4-hydroxy-2,3-dimethoxy-6-methyl-5(3,7,11-trimethyl-dodeca-2,6,10-trienyl)-cyclohex-2-enone purified from example 1 of the present invention on HbsAg synthesis. The compound 4-hydroxy-2,3-dimethoxy-6-methyl-5(3,7,11-trimethyl-dodeca-2,6,10-trienyl)-cyclohex-2-enone could effectively inhibit the synthesis of HbsAg in comparison to the crude extracts of *Antrodia camphorata* in control group, and HbsAg levels decreased with the increase amount of cyclohexenone. Synthesis of HbsAg was decreased to below 60% when treated with 0.1 µg/ml of cyclohexenone from *Antrodia camphorata*. The decrease of HbsAg could reach to as low as 28% when treated with 10 µg/ml of cyclohexenone from *Antrodia camphorata*, which showed the best inhibitory effect. Therefore, it has been proved that the compound 4-hydroxy-2,3-dimethoxy-6-methyl-5(3,7,11-trimethyl-dodeca-2,6,10-trienyl)-cyclohex-2-enone could indeed decrease the synthesis of HbsAg, and it also has inhibitory effect on HBV propagation.

Refer to FIG. 3, the effects of 4-hydroxy-2,3-dimethoxy-6-methyl-5(3,7,11-trimethyl-dodeca-2,6,10-trienyl)-cyclohex-2-enone purified from example 1 of the present invention on HbeAg synthesis. The compound 4-hydroxy-2,3-dimethoxy-6-methyl-5(3,7,11-trimethyl-dodeca-2,6,10-trienyl)-cyclohex-2-enone could effectively inhibit the synthesis of HbeAg in comparison to the crude extracts of *Antrodia camphorata* in control group. Synthesis of HbeAg was decreased to below 84% when treated with 0.1 µg/ml of cyclohexenone from *Antrodia camphorata*. The decrease of HbeAg could reach to as low as 57% when treated with 1 µg/ml of cyclohexenone from *Antrodia camphorata*, which showed the best inhibitory effect. Therefore, it has been proved that the compound 4-hydroxy-2,3-dimethoxy-6-methyl-5(3,7,11-trimethyl-dodeca-2,6,10-trienyl)-cyclohex-2-enone could indeed decrease the synthesis of HbeAg.

On the other hand, the inhibitory effects of cyclohexenone compound from *Antrodia camphorata* in synthesis of HbsAg and HbeAg are larger than that in cytotoxicity test of HepG2 2.2.1 cells. This represents toxicity to cells due to the inhibitory effects of the compound 4-hydroxy-2,3-dimethoxy-6-methyl-5(3,7,11-trimethyl-dodeca-2,6,10-trienyl)-cyclohex-2-enone in the synthesis of HbsAg and HbeAg.

In summary, the compound 4-hydroxy-2,3-dimethoxy-6-methyl-5(3,7,11-trimethyl-dodeca-2,6,10-trienyl)-cyclohex-2-enone isolated from *Antrodia camphorata* according to the present invention can be used to effectively inhibit the survival rate of human hepatoma cell HepG2 2.2.1, and can inhibit the synthesis of HbsAg and HBeAg. Therefore, these compounds can inhibit the duplication and secretion of HBV, and can be used in treatment of HBV-related liver diseases. In addition, it can be incorporated into pharmaceutical compositions. The pharmaceutical compositions include not only the active compound 4-hydroxy-2,3-dimethoxy-6-methyl-5 (3,7,11-trimethyl-dodeca-2,6,10-trienyl)-cyclohex-2-enone, but also the pharmaceutically accepted carries. Examples of such carriers include, but are not limited to, excipients such as water, fillers such as sucrose or starch, binders such as cellulose derivatives, diluents, disintegrants, absorption enhancers or sweeteners. The composition of the present invention can be manufactured through mixing the compound of cyclohexenone from *Antrodia camphorata* with at least one of the carriers by means of conventional methods known in the pharmaceutically technical field, which can be formulated in the forms of powder, tablets, capsules, pellets, granules or other liquid formulation, but are not limited to.

What is claimed is:

1. A method for the treatment of HBV-induced diseases which comprises administering to a subject in need thereof an effective amount of a cyclohexenone compound of *Antrodia camphorata* having the following formula:

wherein X and Y is oxygen or sulfur, $R_1$, $R_2$ and $R_3$ are each a hydrogen atom, methyl or $(CH_2)_m$—$CH_3$, and m=1-12; n=1-12.

2. The method as claimed in claim 1, wherein the compound is isolated from the organic solvent extracts of *Antrodia camphorata*.

3. The method as claimed in claim 2, wherein the organic solvents are selected from the group consisting of alcohols, esters, alkanes, or halogenated alkanes.

4. The method as claimed in claim 3, wherein the alcohol is ethanol.

5. The method as claimed in claim 1, wherein the compound is isolated from the aqueous extracts of *Antrodia camphorata*.

6. The method as claimed in claim 1, wherein the compound is 4-hydroxy-2,3-dimethoxy-6-methyl-5(3,7,11-trimethyl-dodeca-2,6,10-trienyl)-cyclohex-2-enone.

7. The method as claimed in claim 1, wherein the compound inhibit HBV through decrease the synthesis of HbsAg and HbeAg.

8. The method as claimed in claim 7, wherein the preferred concentration of the compound in decreasing HbsAg is 10 µg/ml.

9. The method as claimed in claim 7, wherein the preferred concentration of the compound in decreasing HbeAg is 1 µg/ml.

10. The method as claimed in claim 6, wherein the compound inhibit HBV through decrease the synthesis of HbsAg and HbeAg.

11. The method as claimed in claim 10, wherein the preferred concentration of the compound in decreasing HbsAg is 10 µg/ml.

12. The method as claimed in claim 10, wherein the preferred concentration of the compound in decreasing HbeAg is 1 µg/ml.

* * * * *

UNITED STATES PATENT AND TRADEMARK OFFICE
CERTIFICATE OF CORRECTION

PATENT NO.        : 7,411,003 B1
APPLICATION NO.   : 11/842795
DATED             : August 12, 2008
INVENTOR(S)       : Ai Qun Liu et al.

It is certified that error appears in the above-identified patent and that said Letters Patent is hereby corrected as shown below:

At column 3, lines 7-19, Formula (1) should be corrected to:

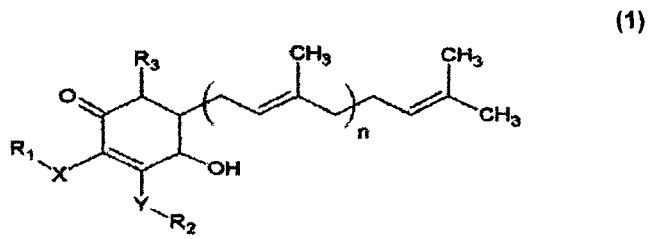

(1)

Claim 1, at column 8, lines 42-52, the formula should be corrected to:

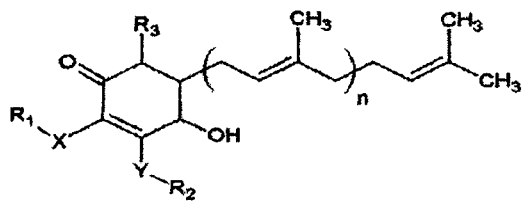

Signed and Sealed this
Twelfth Day of April, 2011

David J. Kappos
*Director of the United States Patent and Trademark Office*